United States Patent
Dondysh

(10) Patent No.: US 7,044,922 B1
(45) Date of Patent: May 16, 2006

(54) NON-INVASIVE DIAGNOSTIC APPARATUS AND METHOD COMPRISING A CEREBRAL STETHOSCOPE FOR DETECTING CEREBROVASCULAR DISEASE

(76) Inventor: Leon Michael Dondysh, P.O. Box 234, Alpine, NJ (US) 07620

( * ) Notice: Subject to any disclaimer, the term of this patent is extended or adjusted under 35 U.S.C. 154(b) by 0 days.

(21) Appl. No.: 11/025,089

(22) Filed: Dec. 29, 2004

(51) Int. Cl.
*A61B 7/00* (2006.01)

(52) U.S. Cl. ..................................................... 600/586
(58) Field of Classification Search ................ 600/586, 600/528; 381/67; 181/131
See application file for complete search history.

(56) References Cited

U.S. PATENT DOCUMENTS

| | | |
|---|---|---|
| 4,008,711 A | 2/1977 | Olinger et al. |
| 4,202,348 A | 5/1980 | Abe et al. |
| 4,220,160 A | 9/1980 | Kimball et al. |
| 4,226,248 A | 10/1980 | Manoli |
| 4,239,047 A | 12/1980 | Griggs, III et al. |
| 4,295,471 A | 10/1981 | Kaspari |
| 4,438,772 A | 3/1984 | Slavin |
| 4,594,731 A | 6/1986 | Lewkowicz |
| 4,720,866 A | 1/1988 | Elias et al. |
| 4,723,555 A | 2/1988 | Shue |
| 4,783,813 A | 11/1988 | Kempka |
| 4,783,814 A | 11/1988 | Foley |
| 4,862,361 A | 8/1989 | Gordon et al. |
| 4,928,705 A | 5/1990 | Sekhar et al. |
| 4,986,276 A | 1/1991 | Wright |
| 5,010,889 A | 4/1991 | Bredesen et al. |
| 5,036,857 A | 8/1991 | Semmlow et al. |
| 5,218,969 A | 6/1993 | Bredesen et al. |
| 5,267,565 A | 12/1993 | Beard |
| 5,305,753 A | 4/1994 | Wilson |
| 5,327,893 A | 7/1994 | Savid |
| 5,441,051 A | 8/1995 | Hileman et al. |
| 5,473,948 A | 12/1995 | Moss et al. |
| 5,717,769 A | 2/1998 | Williams |
| 5,825,895 A | 10/1998 | Grasfield et al. |
| 5,844,995 A | 12/1998 | Williams |
| 5,844,997 A | 12/1998 | Murphy, Jr. |
| 5,882,302 A | 3/1999 | Driscoll, Jr. et al. |
| 5,909,495 A | 6/1999 | Andrea |
| 5,993,389 A | 11/1999 | Driscoll, Jr. et al. |
| 6,002,777 A * | 12/1999 | Grasfield et al. ............. 381/67 |
| 6,112,108 A | 8/2000 | Tepper et al. |
| 6,193,668 B1 | 2/2001 | Chassaing et al. |
| 6,295,365 B1 | 9/2001 | Ota |
| 6,396,931 B1 | 5/2002 | Malilay |
| 6,415,033 B1 | 7/2002 | Halleck et al. |
| 6,428,478 B1 | 8/2002 | Redano |
| 6,454,045 B1 | 9/2002 | Ryan |

(Continued)

*Primary Examiner*—Max F. Hindenburg
*Assistant Examiner*—Brian Szmal
(74) *Attorney, Agent, or Firm*—Richard M. Goldberg

(57) ABSTRACT

A non-invasive apparatus for detecting turbulent flow in a cerebrovascular system of a patient without use of software, includes a planar, circular head adapted to be placed against an eye socket of the patient. A microphone in the head detects an acoustic signal from the cerebrovascular system and converts the acoustic signal to an electrical signal. A filter passes only a portion of the electrical signal having a frequency in a range between 350 Hz and 1,800 Hz as a filtered electrical signal, so as to eliminate extraneous signals due to other than vascular flow. A headset has at least one ear piece with a speaker therein for converting the filtered electrical signal to an audio signal in order to detect the turbulent flow in the cerebrovascular system of the patient.

17 Claims, 2 Drawing Sheets

U.S. PATENT DOCUMENTS

| | | |
|---|---|---|
| 6,512,830 B1 | 1/2003 | Orten |
| 6,544,181 B1 | 4/2003 | Buck et al. |
| 6,626,838 B1 | 9/2003 | Doten et al. |
| 6,692,443 B1 | 2/2004 | Crutchfield et al. |
| 6,699,193 B1 | 3/2004 | Crutchfield et al. |
| 6,723,051 B1 | 4/2004 | Davidson et al. |
| 6,816,743 B1 | 11/2004 | Moreno et al. |
| 2003/0002685 A1* | 1/2003 | Werblud ............ 381/67 |

* cited by examiner

NON-INVASIVE DIAGNOSTIC APPARATUS AND METHOD COMPRISING A CEREBRAL STETHOSCOPE FOR DETECTING CEREBROVASCULAR DISEASE

BACKGROUND OF THE INVENTION

The present invention relates generally to a non-invasive apparatus and method for detecting blood flow in the vascular system for the purpose of detecting vascular pathology.

Cerebrovascular disease is the most common neurological disorder. Cerebrovascular disease is the major cause of hospitalization. For example, there are 500,000 new patients with strokes each year in the United States, and each year, strokes kill 175,000 people and disable 200,000 people in the United States.

Pathological changes in brain vessels begin years before the dramatic stroke kills or paralyzes a person. When a physician sends a patent for angiography, an MRI or a CAT scan, it is often too late. In this regard, it is desirable to provide a quick diagnosis in an emergency room and in private practice to detect cerebrovascular problems at an early stage.

Various auscultation devices are known which are capable of listening to sounds arising within organs as an aid to diagnosis and treatment. Such devices aid a doctor in providing a correct diagnosis by providing more detailed and specific sound information than is possible using an ordinary stethoscope. Further, such devices often permit the recording, processing and displaying of various characteristics of the captured sounds.

However, none of these devices are designed to detect cerebrovascular pathology.

For example, U.S. Pat. No. 4,008,711 to Olinger et al, discusses the detection of aneurysms where the frequency range is 200 Hz to 800 Hz, using computerized models on a Hewlett Packard fourier analyzer model 5451. It is known that a frequency range from human organs is a constant physiological value between 10 Hz and 300 Hz. In like manner, U.S. Pat. No. 4,928,705 to Sekhar et al discloses an acoustic aneurysm detector which uses hydrophonic sensors implanted in a helmet and which make contact with the skull. However, the preferred frequency range is 100 Hz to 1,000 Hz and Sekhar et al uses an EKG and computer.

SUMMARY OF THE INVENTION

Accordingly, it is an object of the present invention to provide a non-invasive apparatus and method for detecting turbulent flow in the cerebrovascular system.

It is another object of the present invention to provide such a non-invasive apparatus and method for the purpose of detecting cerebrovascular problems at an early stage of development.

It is yet another object of the present invention to provide such a non-invasive apparatus and method for the purpose of detecting cerebrovascular problems including detecting occluded arteries, constricted cerebral blood vessels, aneurysms and arteriovenous malformations.

It is a yet further object of the present invention to provide such a non-invasive apparatus and method that is economical and easy to use.

In accordance with an aspect of the present invention, a non-invasive apparatus for detecting turbulent flow in a cerebrovascular system of a patient, includes a stethoscope head adapted to be placed against a body of the patient; a first transducer in the head for detecting an acoustic signal from a cerebrovascular system of the patient and converting the acoustic signal to an electrical signal; a filter for passing only a portion of the electrical signal having a frequency in a range between 350 Hz and 1,800 Hz as a filtered electrical signal, so as to eliminate extraneous signals due to other than cerebrovascular flow; a headset having at least one ear piece; and a second transducer for converting the filtered electrical signal to an audio signal and supplying the audio signal to the headset in order to detect the turbulent flow in the cerebrovascular system of the patient.

The first transducer includes a microphone, while the second transducer includes a speaker. Preferably, the filter includes a low pass filter which only passes electrical signals having frequencies less than 1,800 Hz, and a high pass filter connected in series with the low pass filter between the first and second transducers and which only passes frequencies greater than 350 Hz. Further, at least one amplifier amplifies the electrical signal.

A switch can selectively switch between the filtered electrical signal and an unfiltered electrical signal which bypasses the filter, and will supply the switched signal to the second transducer.

There is further provided a manually adjustable volume control for adjusting a strength of the signal supplied to the second transducer, and an amplifier which frequency multiples the electrical signal from the switch into a range that will be audible when converted to an audio signal by the second transducer.

A binaural connecting lead has one end connected to the head, a yoke is connected to the headset, and an electrical casing for holding the filter is connected between the binaural connecting lead and the yoke.

Preferably, a plateau is mounted to one side of the head, and holding pieces are mounted to the plateau such that a person can hold the head to the body of the patient by the holding pieces without the microphone picking up acoustic signals from the person holding the holding pieces. The head preferably has a generally planar configuration, and the holding pieces include elements extending from opposite sides of the plateau. More specifically, the head has a generally planar, circular configuration such that the head can be held against an eye socket of the patient to detect cerebrovascular problems.

In accordance with another aspect of the present invention, a non-invasive method for detecting turbulent flow in a cerebrovascular system of a patient, includes the steps of detecting an acoustic signal from a cerebrovascular system of the patient; converting the acoustic signal to an electrical signal; filtering the electrical signal by the step of passing only a portion of the electrical signal having a frequency in a range between 350 Hz and 1,800 Hz as a filtered electrical signal, so as to eliminate extraneous signals due to other than vascular flow; converting the filtered electrical signal to an audio signal; and supplying the audio signal to a headset in order to detect the turbulent flow in the cerebrovascular system of the patient.

The above and other objects, features and advantages of the invention will become readily apparent from the following detailed description thereof which is to be read in connection with the accompanying drawings.

DETAILED DESCRIPTION

In accordance with the present invention, a non-invasive apparatus 10 is provided for detecting turbulent flow in the cerebrovascular system, for the purpose of detecting cerebrovascular pathology. Specifically, apparatus 10 examines acoustic signals having frequencies in the range of 350 Hz and 1,800 Hz, while filtering out other signals.

Specifically, when using the present invention, partially occluded arteries, aneurysms, arteriovenous malformations and the like, will result in a bruit or roaring sound being produced.

Figure 1:
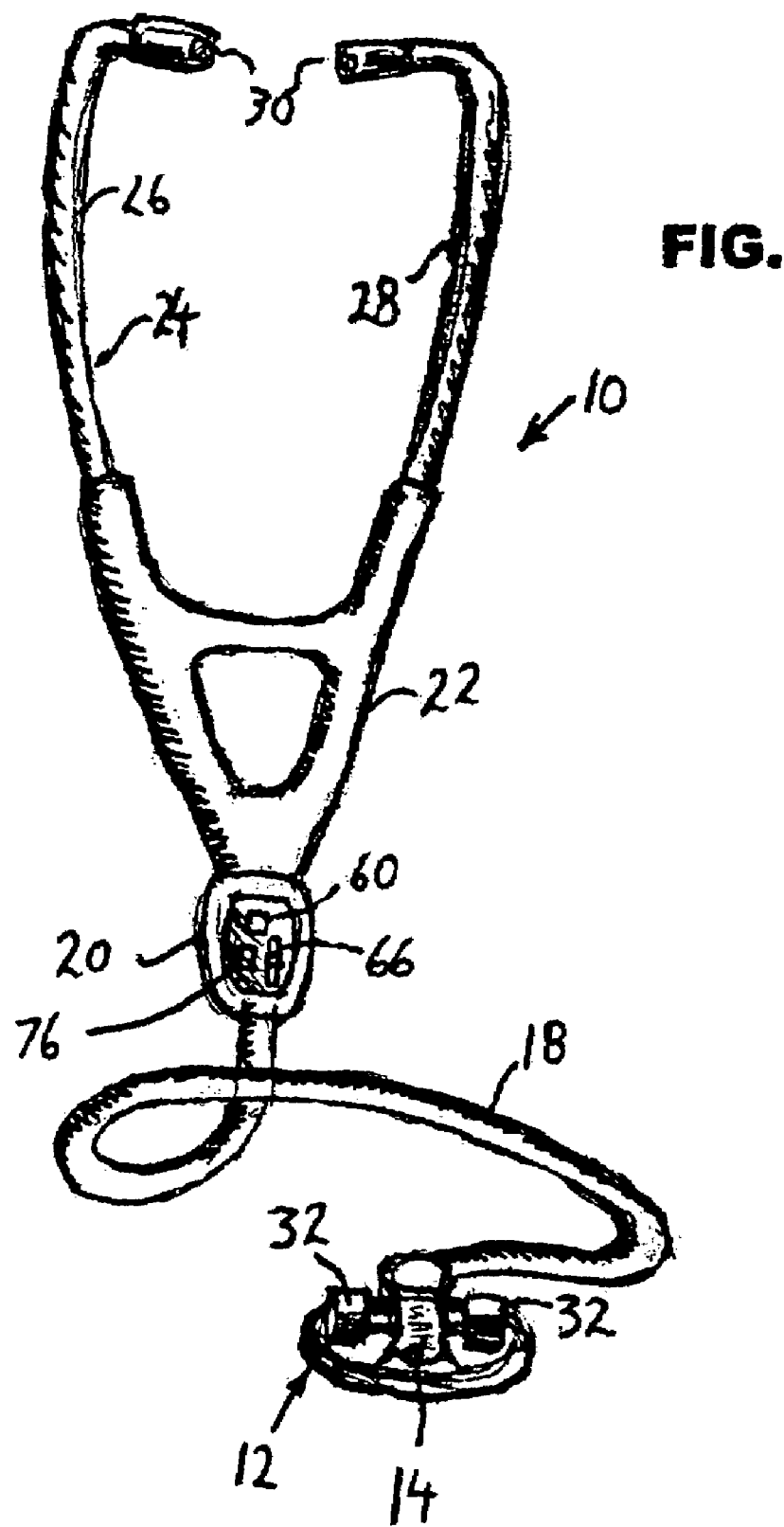
FIG. 1 is a perspective view of a non-invasive apparatus and method for detecting turbulent flow in the cerebrovascular system according to an embodiment of the present invention.

Referring to the drawings in detail, and initially to FIG. 1, non-invasive apparatus 10, in a preferred embodiment, is formed by a stethoscope having a flat, circular-shaped stethoscope head 12 with a plateau 14 connected on one surface thereof. A microphone 16, which can be a bell-type and/or diaphragm-type microphone, is contained within plateau 14 for receiving vibrating signals from the human body and converting these signals into electrical signals. A binaural connecting lead 18 is connected to plateau 14 and microphone 16 for receiving the transduced electrical signals from microphone 16 and carrying the transduced electrical signal to electronic circuitry in an electronic casing 20 at the opposite end of binaural connecting lead 18. As will be discussed in more detail hereinafter, the electronic circuitry processes the transduced electrical signal to pass only that part of the signal having frequencies in the range of 350 Hz to 1,800 Hz.

A yoke 22 is connected with the electronic circuitry in electronic casing 20 and supplies the processed electrical signal to a headset 24 having dual sound transmitting tubes 26 and 28, each of which terminate in ear tips 30.

However, the apparatus will generate irrelevant frequencies, which derive from a doctor's fingers (muscles) when the device is held by the doctor and applied onto the anatomical windows. The frequency range of such signals is approximately 100 Hz and may fall within the filtered range of the invention. To eliminate signals with these frequencies, an extra approximately one centimeter of hard rubber or plastic coating (4.5 centimeters in diameter) is added to plateau 14. The same material is also used to create two extensions 32 which extend from opposite sides of plateau 14 by which a person can hold onto stethoscope head 12 and apply the same against a patient's body by the distal phalanges of the fingers, and particularly, the thumb and index finger. This provides that any sounds from the doctor's hand are not picked up by microphone 16, which could otherwise occur if the doctor directly handled stethoscope head 12.

Figure 2:
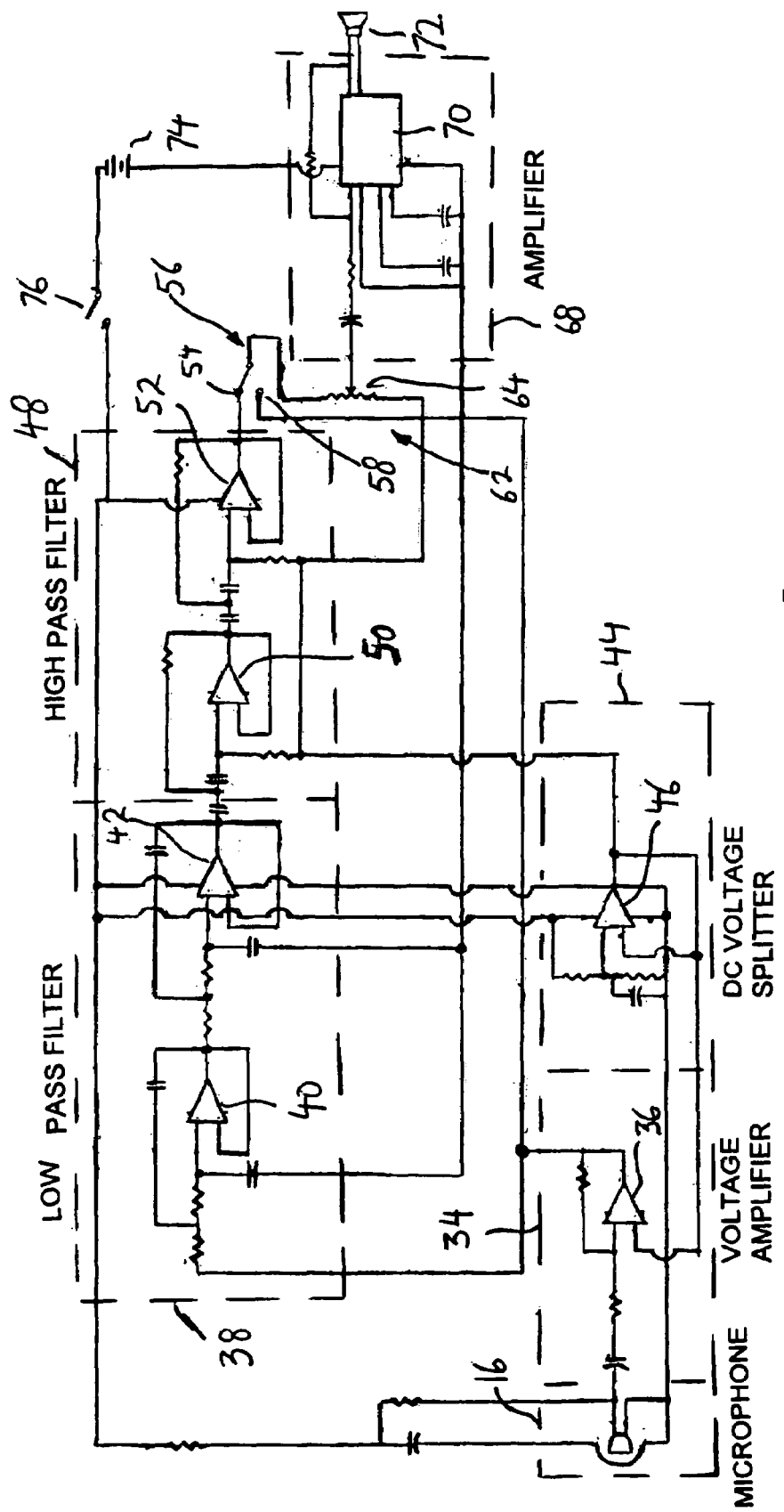
FIG. 2 is a circuit wiring diagram of the circuitry used with the apparatus of FIG. 1.

Referring now to FIG. 2, there is shown a preferred embodiment of the circuit wiring diagram of the circuitry held within electronic casing 20.

Specifically, microphone 16 converts detected physical vibrations into a transduced AC electrical signal. The AC signal from microphone 16 is supplied through a series circuit of a capacitor and resistor to a wide frequency band voltage amplifier 34, formed, for example, by a type OP270 dual very low noise precision operational amplifier 36, which amplifies the transduced electrical signal from microphone 16 in a wide band up to 40 dB. The output from voltage amplifier 34 is supplied to the input of a low pass filter 38 formed, for example, from two type OP 270 dual very low noise precision operational amplifiers 40 and 42 connected in series. Preferably, low pass filter 38 is a third order low pass filter. Low pass filter 38 functions to filter out or cut off signals having frequencies greater than 1,800 Hz, and thereby pass through signals less than or equal to 1,800 Hz.

A direct current (DC) voltage splitter 44 is also connected with an output of microphone 16 and is formed by a dual very low noise precision operational amplifier 46. The output of DC voltage splitter 44 is input to a control input of operational amplifier 42 of low pass filter 38 to provide correct operation thereof.

The output from low pass filter 38 is supplied to the input of a high pass filter 48 formed, for example, from two type OP 270 dual very low noise precision operational amplifiers 50 and 52 connected in series. Preferably, high pass filter 48 is a fourth order high pass filter. High pass filter 48 functions to filter out or cut off signals having frequencies less than 350 Hz, and thereby pass through signals greater than or equal to 350 Hz. In this regard, the combination of low pass filter 38 and high pass filter 48 functions to pass through those signals having frequencies in the range of 350 Hz to 1,800 Hz.

The output from high pass filter 48 is supplied to one input 54 of a switch 56. The other input 58 of switch 56 is supplied with the unfiltered output from voltage amplifier 36. Although switch 56 is shown as a single pole double throw switch, this is for illustration only, and the present invention is not limited thereby. Switch 56 is adapted to pass either the filtered signal from high pass filter 48 in order to use the apparatus for detecting cerebrovascular disease, or the unfiltered signal from voltage amplifier 36, in which case the apparatus is used as a conventional electronic stethoscope. A toggle switch 60 or the like on electronic casing 20 can be activated to switch between inputs 54 and 58.

The output from switch 56 is supplied to a volume control 62 formed by a variable resistor 64 to vary the power from 0 to 100 μwatts, thereby effectively varying the sound pressure level (SPL) up to 105 dB. Volume control switch 62 can be adjusted by a slide switch 66 on electronic casing 20.

The output from volume control 62 is supplied to an amplifier 68 which frequency multiples the electrical signal into a range that will be audible when converted to an audio signal. Preferably, amplifier 68 is formed by a type MC34119 low power audio amplifier 70, although the present invention is not limited thereto. The output from amplifier 68 is supplied to a speaker 72 which transduces the electrical signal to an audio signal that is supplied to yoke 22 and headset 24.

A battery 74 is connected to various components for supplying power to the circuitry, and an ON/OFF switch 76 is connected with battery 74 to turn the circuitry ON and OFF. ON/OFF switch 76 can be provided on electronic casing 20.

In this manner, when detecting cerebrovascular disease, switch 56 is switched to transmit the filtered signal from input 54. In such case, stethoscope head 12 is placed over the patient's eye, and only those signals relating to turbulent vascular flow are heard, whereby the physician can detect abnormalities in the vascular flow, such as partially occluded cerebral arteries, arteriospasms, arteriostenosis, aneurysms, arteriovenous malformations and the like. Stethoscope head 12 can be held at the orbital (ophthalmic) left or right side of the patient's head, the temporal left or right side, the sub-occipital, maximum proximate to the foramen magnum or the abow cervical bifurcation of the common carotid artery at the left or right side. Specifically, in such case, turbulent flow in the cerebral vascular system, is produced as a higher frequency sound than with laminar blood flow, which is a normal condition. When the sound changes to a higher frequency sound, this means that the detected audio signals are the range of approximately 350 Hz to 1,800 Hz. External sounds are filtered and do not thereby affect the operation. Further, in such case, since the physician holds stethoscope head 12 by screw-in bolts 32, any sound from the physician's body is not detected by microphone 16, thereby providing a more accurate analysis.

When switch 56 is switched to transmit the unfiltered signal from input 58, the apparatus is used as a conventional electronic stethoscope.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

What is claimed is:

1. A non-invasive apparatus for detecting turbulent flow in a cerebrovascular system of a patient, comprising:
    a stethoscope head adapted to be placed against a body of the patient;
    a first transducer in said head for detecting an acoustic signal from a cerebrovascular system of the patient and converting said acoustic signal to an electrical signal;
    a filter for passing only a portion of said electrical signal having a frequency in a range only between 350 Hz and 1,800 Hz as a filtered electrical signal and preventing passing of any signals less than 350 Hz and any signals greater than 1,800 Hz, so as to eliminate extraneous signals due to other than cerebrovascular flow;
    a headset having at least one ear piece; and
    a second transducer for converting said filtered electrical signal to an audio signal and supplying said audio signal to said headset in order to detect said turbulent flow in the cerebrovascular system of the patient.

2. A non-invasive apparatus according to claim 1, wherein said first transducer includes a microphone.

3. A non-invasive apparatus according to claim 1, wherein said second transducer includes a speaker.

4. A non-invasive apparatus according to claim 1, wherein said filter includes a low pass filter which only passes electrical signals having frequencies less than 1,800 Hz, and a high pass filter connected in series with said low pass filter between said first and second transducers and which only passes frequencies greater than 350 Hz.

5. A non-invasive apparatus according to claim 1, further comprising at least one amplifier for amplifying said electrical signal.

6. A non-invasive apparatus according to claim 1, further comprising a switch for selectively switching between said filtered electrical signal and an unfiltered electrical signal which bypasses said filter, and supplying the switched signal to said second transducer.

7. A non-invasive apparatus according to claim 6, further comprising a manually adjustable volume control for adjusting a strength of the signal supplied to said second transducer.

8. A non-invasive apparatus according to claim 7, further comprising an amplifier which frequency multiples the electrical signal from the switch into a range that will be audible when converted to an audio signal by said second transducer.

9. A non-invasive apparatus according to claim 1, further comprising:
    a binaural connecting lead having one end connected to said head;
    a yoke connected to said headset; and
    an electrical casing for holding said filter connected between said binaural connecting lead and said yoke.

10. A non-invasive apparatus according to claim 1, wherein said head has a generally planar, circular configuration such that said head can be held against an eye socket of the patient to detect cerebrovascular problems.

11. A non-invasive apparatus for detecting turbulent flow in a cerebrovascular system of a patient, comprising:
    a stethoscope head adapted to be placed against a body of the patient;
    a first transducer in said head for detecting an acoustic signal from a cerebrovascular system of the patient and converting said acoustic signal to an electrical signal;
    a filter for passing only a portion of said electrical signal having a frequency in a range between 350 Hz and 1,800 Hz as a filtered electrical signal, so as to eliminate extraneous signals due to other than vascular flow;
    a headset having at least one ear piece;
    a second transducer for converting said filtered electrical signal to an audio signal and supplying said audio signal to said headset in order to detect said turbulent flow in the cerebrovascular system of the patient;
    a plateau mounted to one side of said head; and
    holding pieces mounted to said plateau such that a person can hold said head to the body of the patient by the holding pieces without the microphone picking up acoustic signals from the person holding the holding pieces.

12. A non-invasive apparatus according to claim 11, wherein said head has a generally planar configuration, and said holding pieces include elements extending from opposite sides of said plateau.

13. A non-invasive method for detecting turbulent flow in a cerebrovascular system of a patient, comprising the steps of;
    detecting an acoustic signal from a cerebrovascular system of the patient;
    converting said acoustic signal to an electrical signal;
    filtering said electrical signal by the step of passing only a portion of said electrical signal having a frequency only in a range between 350 Hz and 1,800 Hz as a filtered electrical signal and preventing passing of any signals less than 350 Hz and any signals greater than 1,800 Hz, so as to eliminate extraneous signals due to other than cerebrovascular flow;
    converting said filtered electrical signal to an audio signal; and
    supplying said audio signal to a headset in order to detect said turbulent flow in the cerebrovascular system of the patient.

14. A non-invasive method according to claim 13, further comprising the step of amplifying said electrical signal.

15. A non-invasive method according to claim 13, further comprising the steps of:
    selectively switching between said filtered electrical signal and an unfiltered electrical signal which bypasses said filter; and
    supplying the switched signal to said second transducer.

16. A non-invasive method according to claim 15, further comprising the step of manually adjusting a strength of the signal supplied to said second transducer so as to adjust a volume thereof.

17. A non-invasive method according to claim 16, further comprising the step of frequency multiplying the switched electrical signal into a range that will be audible when converted to said audio signal.

* * * * *